(12) United States Patent
Su

(10) Patent No.: US 6,878,116 B2
(45) Date of Patent: Apr. 12, 2005

(54) BLOOD PRESSURE ANALYZER

(76) Inventor: Tsung-Kun Su, 5F., No. 142, Sec. 2, Shintai 5th Rd., Shijr City, Taipei (TW), 221

( * ) Notice: Subject to any disclaimer, the term of this patent is extended or adjusted under 35 U.S.C. 154(b) by 164 days.

(21) Appl. No.: 10/277,669

(22) Filed: Oct. 23, 2002

(65) Prior Publication Data

US 2003/0187361 A1 Oct. 2, 2003

(30) Foreign Application Priority Data

Mar. 26, 2002 (TW) ........................ 91105829 A

(51) Int. Cl.$^7$ ................................ A61B 5/02
(52) U.S. Cl. ...................... 600/485; 600/485
(58) Field of Search ............... 600/481–507, 600/300, 301; 345/530, 531, 536–538, 557, 440, 467; 341/155–172; 712/1, 32–35

(56) References Cited

U.S. PATENT DOCUMENTS

| | | | | |
|---|---|---|---|---|
| 3,713,136 A | * | 1/1973 | Nagy, Jr. ............... | 341/118 |
| 3,750,146 A | * | 7/1973 | Lucas .................... | 341/118 |
| 4,417,234 A | * | 11/1983 | McKenna .............. | 341/141 |
| 4,461,266 A | * | 7/1984 | Hood et al. ........... | 600/494 |
| 4,796,184 A | * | 1/1989 | Bahr et al. ............ | 600/492 |
| 5,103,830 A | * | 4/1992 | Shinomiya ............ | 600/485 |
| 5,134,391 A | * | 7/1992 | Okada .................. | 345/467 |
| 5,243,992 A | * | 9/1993 | Eckerle et al. ........ | 600/503 |

* cited by examiner

Primary Examiner—Max F. Hindenburg
Assistant Examiner—Patricia Mallari
(74) Attorney, Agent, or Firm—Troxell Law Office, PLLC

(57) ABSTRACT

A blood pressure analyzer having an interconnected pressure sensor, a signal processor, a microprocessor, and a display. The microprocessor is also connected to memory and a computer transmission interface. The signal processor including a first signal amplifier, a low pass filter, a second signal amplifier, a high pass filter, a voltage clamp, a comparator, a third signal amplifier, an accumulator circuit, and a crystal oscillator. The analyzed and calculated systolic and diasystolic blood pressure values are shown on the display and, furthermore, accurately represents pulse wave form fluctuations to afford the user a complete understanding of blood pressure conditions and thereby provide physicians a reference for the diagnosis of cardiovascular changes.

6 Claims, 7 Drawing Sheets

| Category | Basic Pulse Wave Form | Pulse Wave Form | Diagnosis |
|---|---|---|---|
| A | ▰ | ▮▮▮▮ | Normal |
| B | ▰ | ▮▮▮▮ | Anemia, hypotension, shock |
| C | ▰ | ▮▮▮▮ | Arteriosclerosis, obesity |
| D | ▰ | ▮▮▮▮ | Cardiac disease |
| E | ▮▮▮ | ▮▮▮ | Arrhythmia |

BLOOD PRESSURE ANALYZER

BACKGROUND OF THE INVENTION

1) Field of the Invention

The invention herein relates to blood pressure analysis devices, specifically a blood pressure analyzer capable of displaying both blood pressure figures and pulse waves.

2) Description of the Prior Art

Blood pressure figures serve as a reference for human physical health condition. This is especially so for hypertensive individuals who must take blood pressure readings regularly to understand blood pressure status and thereby prevent it from becoming too high and medically untreatable with fatal consequences. Referring to FIG. 1, based on clinical tests and analyses, categories of cardiovascular diagnosis such as normal, anemia, hypotension, shock, arteriosclerosis, obesity, heart disease, arrhythmia, and other afflictions each exhibit different pulse wave forms when arterial pressure is measured. Since the various said afflictions have differing blood pressure pulse rates that may be 80 percent higher, when blood pressure is measured, viewing the blood pressure pulse wave forms at the same time assists the assessment of physical condition and provides a reference for physicians in the diagnosis of disease. Conventional sphygmomanometers lack pulse level indication capability and structurally complex instruments equipped with blood pressure pulse wave display capability are inconvenient in terms of portability and utilization. The invention herein provides a blood pressure analyzer that is convenient to use and capable of measuring blood pressure while simultaneously displaying blood pressure pulse levels.

SUMMARY OF THE INVENTION

The primary objective of the invention herein is to provide for measuring and analyzing blood pressure variances, wherein after measured blood pressure level figures are processed, the blood pressure values of systolic pressure and diasystolic pressure are displayed in a graphic representation that shows blood pressure wave forms to facilitate a more complete user understanding of blood pressure conditions and, furthermore, provide physicians a reference in the diagnosis of cardiovascular changes.

DETAILED DESCRIPTION OF THE INVENTION

Figure 1:
FIG. 1 is an illustrated table of corresponding cardiovascular disease and blood pressure pulse wave forms.
Figure 2:
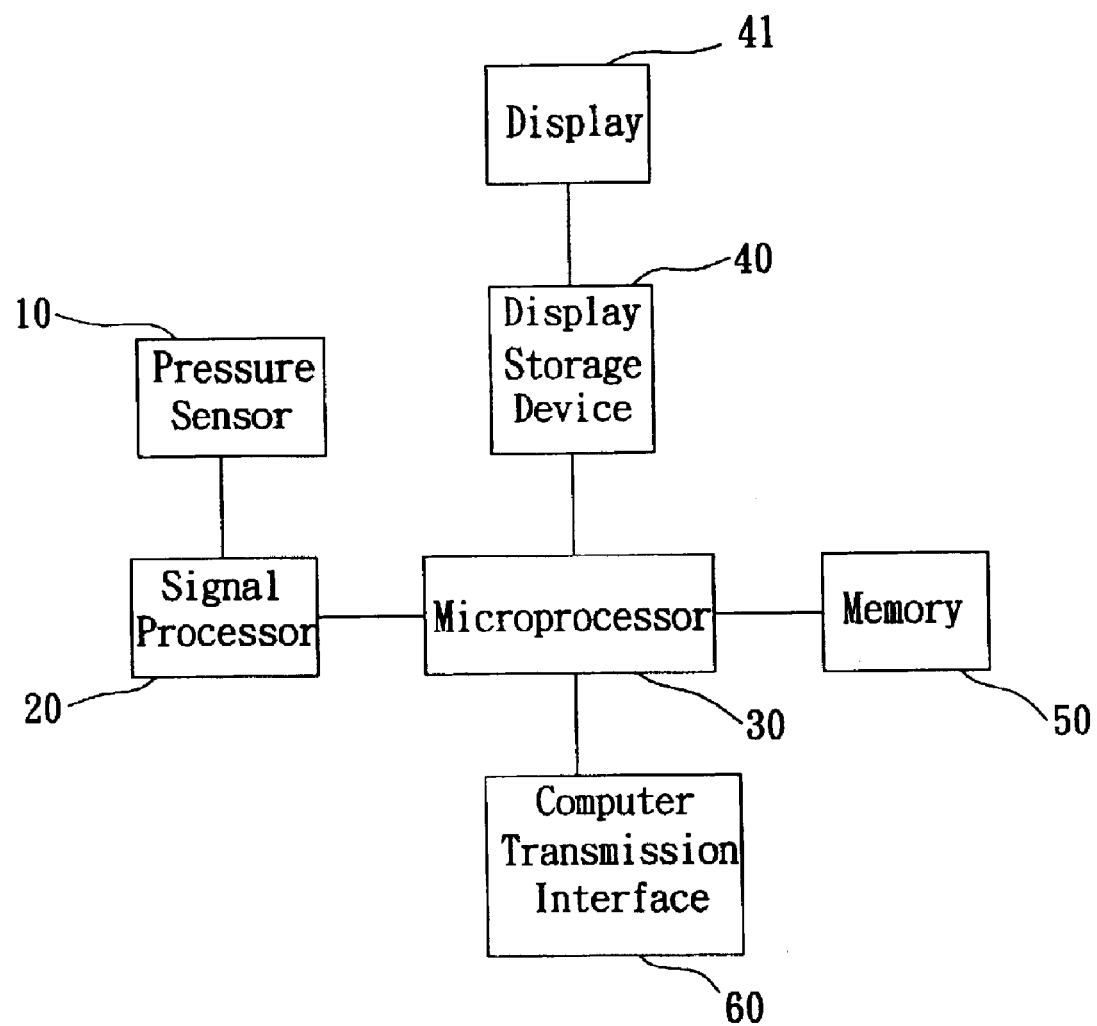
FIG. 2 is a block diagram of the operational structure of the invention herein.
Figure 3:
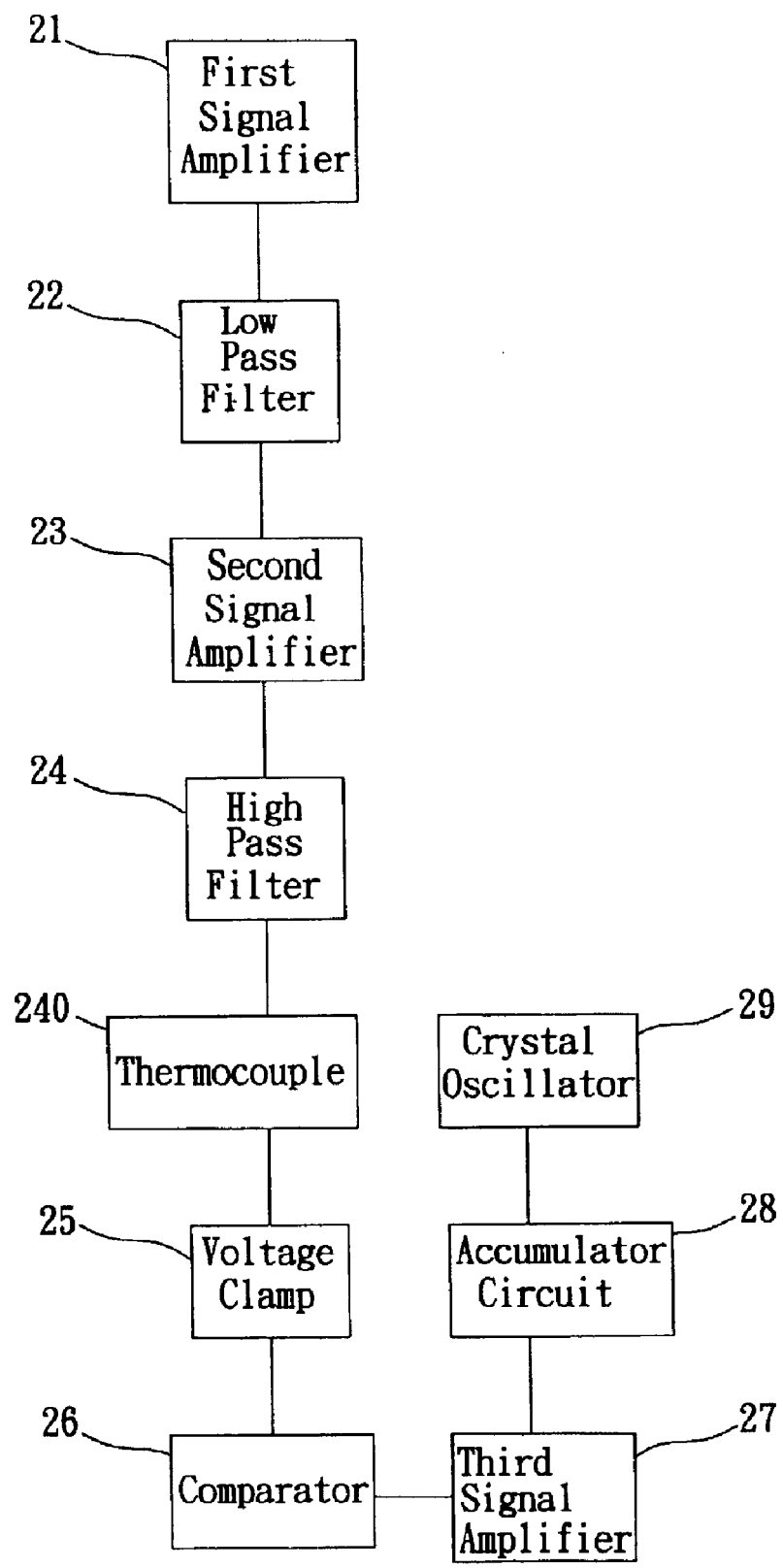
FIG. 3 is a block diagram of the signal processor operational structure of the invention herein.

Referring to FIG. 2 and FIG. 3, the blood pressure analyzer of the invention here is comprised of an interconnected pressure sensor 10, a signal processor 20, a microprocessor 30, a display storage device 40, and a display 41. The said microprocessor 30 is also respectively connected to memory 50 and a computer transmission interface 60. The said signal processor 20 (shown in FIG. 3) consists of a first signal amplifier 21, a low pass filter 22, a second signal amplifier 23, a high pass filter 24, a thermocouple 240, a voltage clamp 25, a comparator 26, a third signal amplifier 27, an accumulator circuit 28, and a crystal oscillator 29.

The invention herein involves the placement of the pressure sensor 10, a thin piezo-conductive pressosensitive element, on a pulsating region of the user. When pressure is applied to the artery, a reaction is produced, at which time the thin piezo-conductive pressosensitive element generates microvolts of voltage. The said voltage is amplified through the first signal amplifier 21 of the signal processor 20 and then processed by the low pass filter 22, the second signal amplifier 23, and the high pass filter 24 to derive the pulse rate and amplify the signal to a level of zero to two volts, with current controlled by the thermocouple 240 according to variances in temperature, thereby regulating the said voltage as the temperature changes; then rise the said voltage by the said voltage clamp 25; the said voltage proceeds to the comparator 26 which in conjunction with the crystal oscillator 29, the accumulator circuit 28, and the third signal amplifier 27 outputs cumulative, triangular wave voltage comparisons that are converted into a high resolution, digital pulse width modulation (PWM) signal values, the said microprocessor 30 controlling the saving into memory 50 of the digital signal values aggregated during the measurement process as well as the calculation of the said digital signal values to obtain the average value, high pressure value, and low pressure value of blood pressure; the microprocessor 30 controls the resolution at which the said digital signal values are outputted and also controls the forwarding of the said various values to the display storage device 40 such that a blood pressure pulse wave graph as well as the blood pressure average value, systolic pressure, and diasystolic pressure values of the user are shown on the display 41; or controls the transfer of the said digital signal values from the computer transmission interface 60 to a personal computer or a hospital computer to serve as an individual's record or reference for medical diagnosis.

Figure 4:
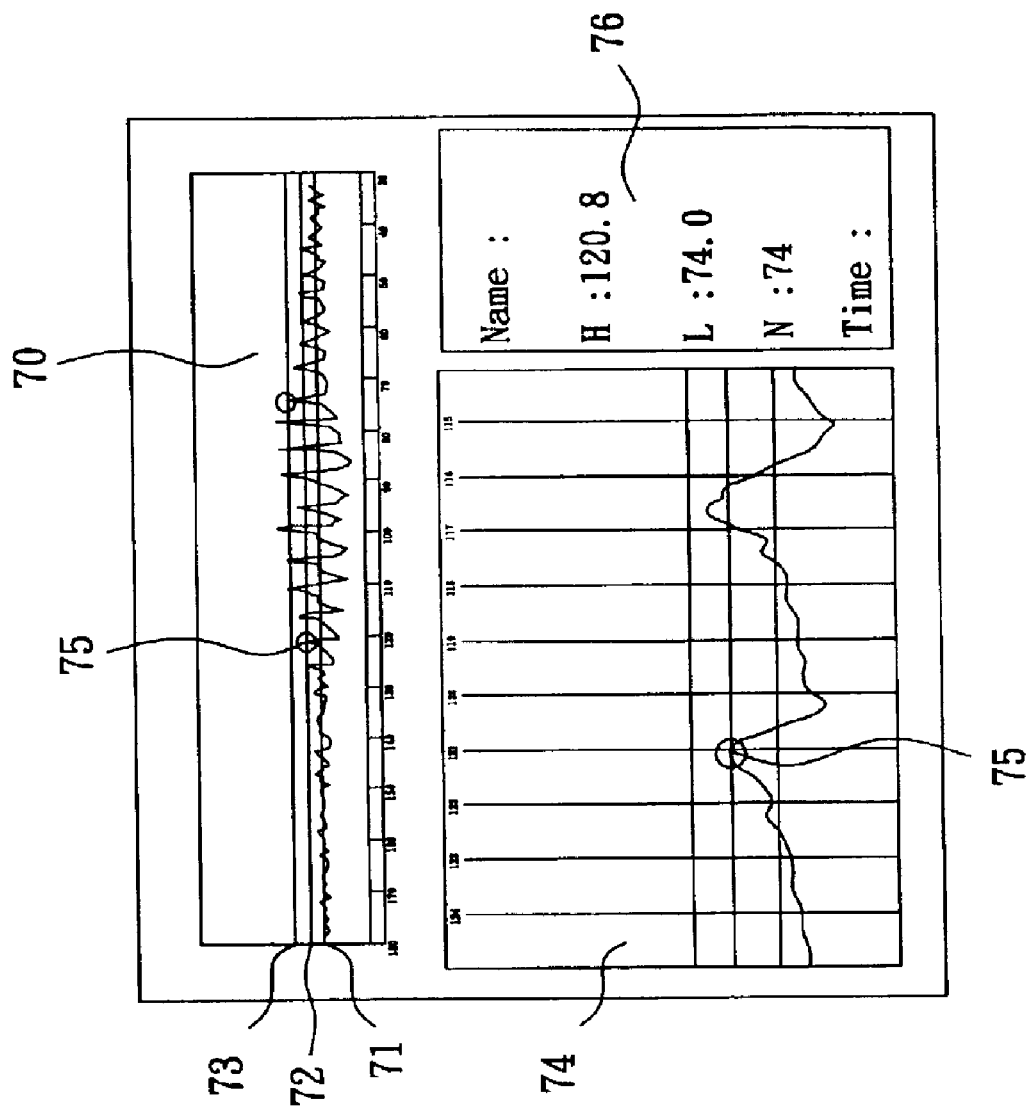
FIG. 4 is a drawing of the first embodiment display of the invention herein.
Figure 5:
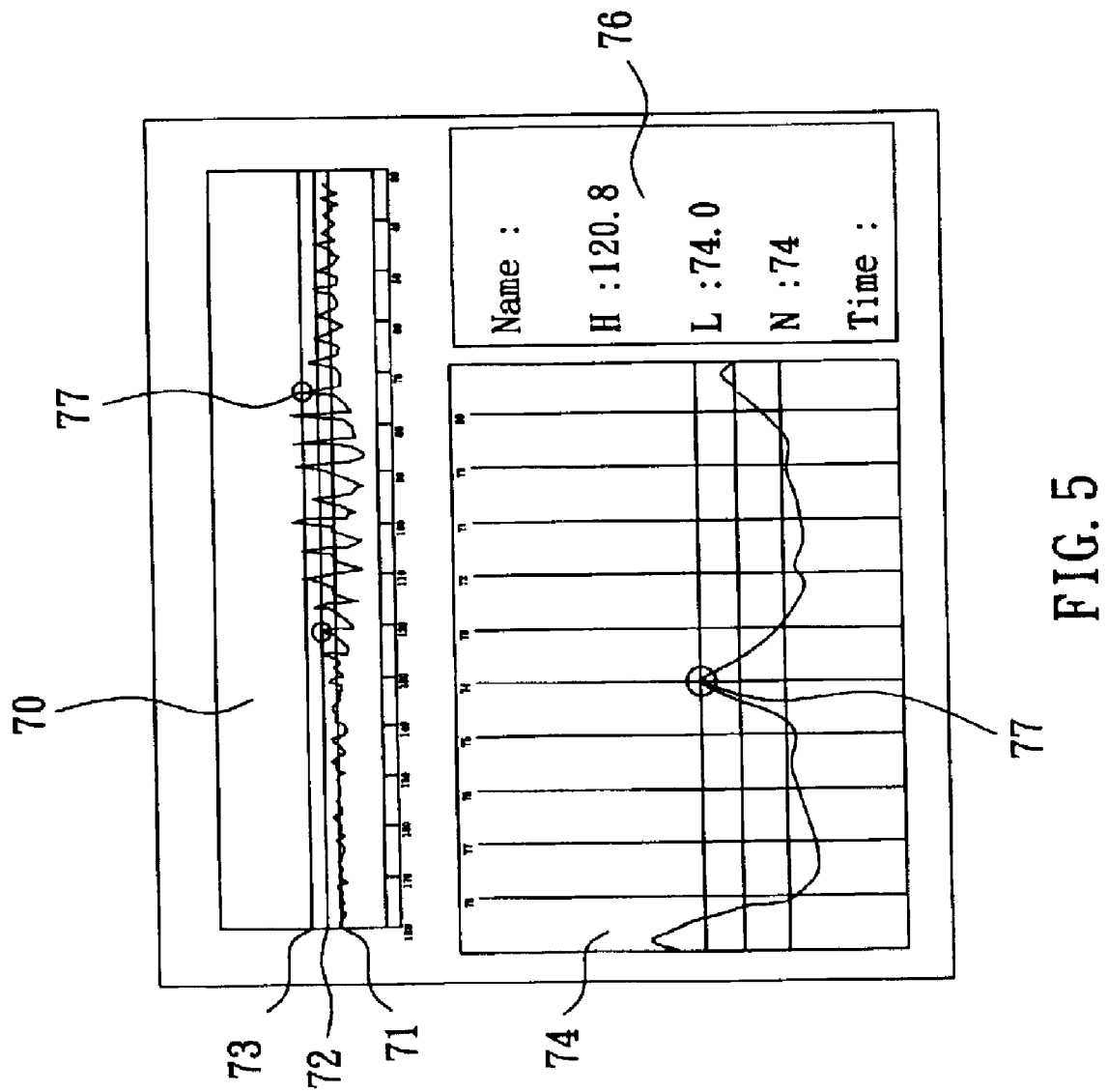
FIG. 5 is a drawing of the second embodiment display of the invention herein.
Figure 6:
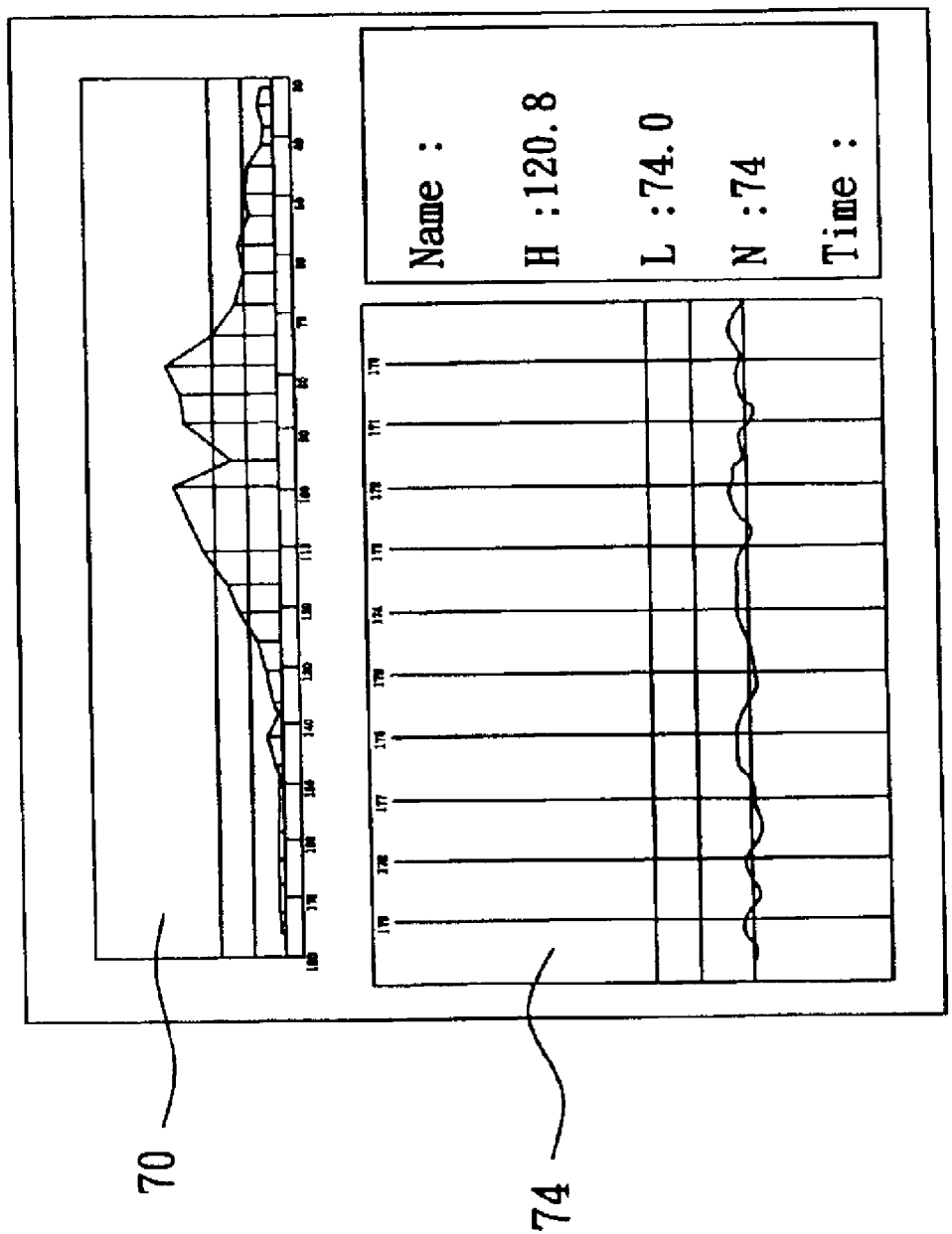
FIG. 6 is a drawing of the third embodiment display of the invention herein.
Figure 7:
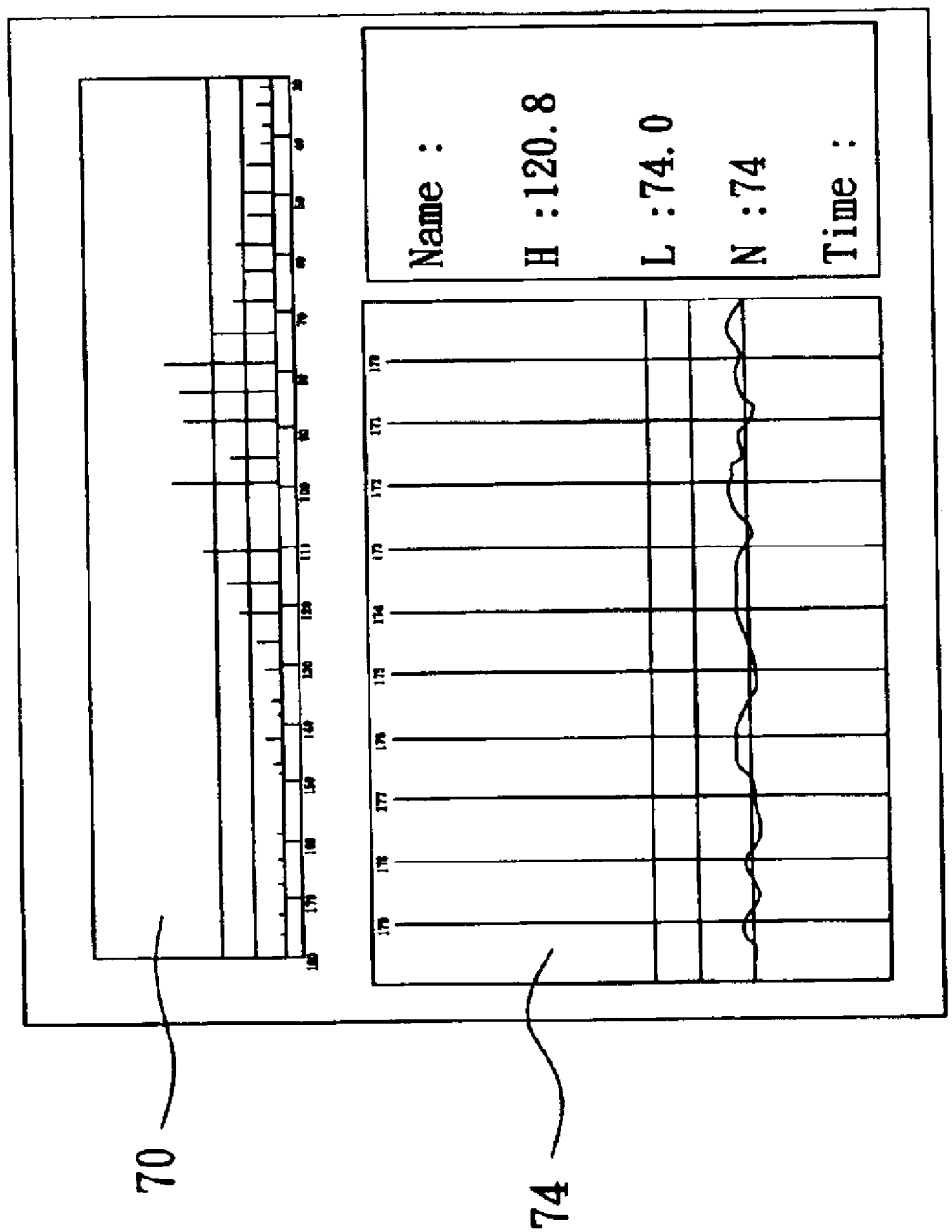
FIG. 7 is a drawing of the fourth embodiment display of the invention herein.

The display 41 of the invention herein shows the systolic and diasystolic blood pressure values as well as the blood pressure arterial wave of the user; as indicated in FIG. 4, the first area 70 shows the blood pressure pulse wave graph of the entire blood pressure measurement process, including the blood pressure average curve 71, the high pressure base curve 72, and the low pressure base curve 73; the second area 74 is a magnified partial view of the first area 71, showing a blood pressure of 120.8 at the high pressure pulse beat position 75 during arterial contraction; and the third area 76 shows the systolic pressure, diasystolic pressure values, pulse count, and other information. FIG. 5 indicates a blood pressure of 74.0 at the low pressure pulse beat position 77 during arterial dilation. FIG. 6 shows graphed representation of blood pressure pulse beat wave peaks. FIG. 7 shows blood pressure pulse waves graphed as columns.

The respective values Pa, Ph, and Pl of the blood pressure average curve, the high pressure base curve, and the low pressure base curve of the invention herein are solved for by the microprocessor 30 in the equation $Pa=(An+A(n+1))/2$, wherein An is the No. n point before the average blood pressure value and $A(n+1)$ is the (n+1) point of the blood pressure value (the high resolution digital signal value), with the calculation of Pa consisting of first sequentially locating all points before the average blood pressure value and then ascertaining the final point of average blood pressure value, the said value being the value of Pa;

taking Pa as a base value, each An point is sequentially integrated once to obtain a respective Kn value and each Kn is compared to Pa, and when a Kn is smaller than Pa, the value of Ph is such that Ph=An, with the systolic pressure point indicated when a single pulse beat value becomes larger than the integrated point of the average blood pressure curve;

taking Pa as a base value, each An point is sequentially differentiated twice to obtain a respective Km value and each Km is compared to Pa, and when a Km is larger than Pa, the value of Pl is such that Pl=An, with the diasystolic pressure point indicated when a single pulse beat value becomes larger than the differentiated point of the average blood pressure curve.

The blood pressure pulse wave data of the invention herein is derived analogically and since there are no resolution limitations, it is capable of displaying blood pressure pulse wave graphs at an even higher resolution and with greater realism. The present invention is not only capable of reading and displaying values of systolic and diasystolic pressure and, furthermore, accurately displaying pulse wave form fluctuations occurring over minute increments of time, but also designed to measure pulse beat levels, shifts in angle, and other data to provide physicians a reference for diagnosing cardiovascular changes.

What is claimed is:

1. A blood pressure analyzer comprising: an interconnected pressure sensor, a signal processor, and a microprocessor, with said microprocessor also connected to memory and said signal processor comprising a first signal amplifier, a low pass filter, a second signal amplifier, a high pass filter, a voltage clamp, a comparator, a third signal amplifier, an accumulator circuit, and a crystal oscillator such that said pressure sensor registers changes in pressure that are converted by said signal processor into high resolution, digital pulse width modulation (PWM) signal values and said microprocessor controls the saving into said memory of the digital signal values aggregated during the measurement process as well as the calculation of said digital signal values to obtain the average value, high pressure value, and low pressure value of blood pressure, wherein said microprocessor executes the equation below to solve for the respective values Pa, Ph, and Pl of the blood pressure average curve, the high pressure base curve, and the low pressure base curve: $Pa=(An+A(n+1))/2$, wherein An is the nth point before the average blood pressure value, and $A(n+1)$ is the (n+1) point of the blood pressure value, with the calculation of Pa consisting of first sequentially locating all points before the average blood pressure value and then ascertaining the final point of the average blood pressure value, said value being the value of Pa;

taking Pa as a base value, each An point is sequentially integrated once to obtain a respective Kn value and each Kn is compared to Pa, and when a Kn is smaller than Pa, the value of Ph is such that Ph=An;

taking Pa as a base value, each An point is sequentially differentiated twice to obtain a respective Km value and each Km is compared to Pa, and when a Km is larger than Pa, the value of P1 is such that P1=An.

2. A blood pressure analyzer as claimed in claim 1 in which said microprocessor is also connected to a display storage device and said display storage device is connected to a display.

3. A blood pressure analyzer as claimed in claim 1 in which said microprocessor is also connected to a computer transmission interface.

4. A blood pressure analyzer comprising: an interconnected pressure sensor, a signal processor, and a microprocessor, with said microprocessor also connected to memory and said signal processor comprising a first signal amplifier, a low pass filter, a second signal amplifier, a high pass filter, a voltage clamp, a comparator, a third signal amplifier, an accumulator circuit, and a crystal oscillator such that said pressure sensor registers changes in pressure that are converted by said signal processor into high resolution, digital pulse width modulation (PWM) signal values and said microprocessor controls the saving into said memory of the digital signal values aggregated during the measurement process as well as the calculation of said digital signal values to obtain the average value, high pressure value, and low pressure value of blood pressure, wherein said high pass filter and said voltage clamp have a thermocouple connected between them such that voltage values outputted from said high pass filter to said voltage clamp are regulated as variances in temperature occur.

5. A blood pressure analyzer as claimed in claim 4 in which said microprocessor is also connected to a display storage device and said display storage device is connected to a display.

6. A blood pressure analyzer as claimed in claim 4 in which said microprocessor is also connected to a computer transmission interface.

* * * * *